(12) United States Patent
Ibrahim

(10) Patent No.: US 6,932,992 B1
(45) Date of Patent: Aug. 23, 2005

(54) COMPOSITION AND METHOD FOR INHIBITION OF HARMFUL BACTERIA

(75) Inventor: Salam Ibrahim, Greenboro, NC (US)

(73) Assignee: North Carolina A&T State University, Greensboro, NC (US)

( * ) Notice: Subject to any disclaimer, the term of this patent is extended or adjusted under 35 U.S.C. 154(b) by 111 days.

(21) Appl. No.: 10/306,616

(22) Filed: Nov. 27, 2002

Related U.S. Application Data

(60) Provisional application No. 60/355,869, filed on Nov. 30, 2001.

(51) Int. Cl.$^7$ ............ A01N 63/00; A01N 65/00; A23L 3/3571
(52) U.S. Cl. ............ 426/61; 426/335; 426/655; 426/574; 424/745
(58) Field of Search ............ 426/61, 335, 542, 426/655, 654, 574, 615; 424/745

(56) References Cited

OTHER PUBLICATIONS http://www.preparedfoods.net/CDA/ArticleInformation/features/BNP_Features_Item/0,1231,114852,00.html "Enzymes, Protectants & Colorings". Write-in article 222, posted on Aug. 1, 2001.*

Lambert, RJW et al. J. Applied Microb. 91(3):453-462; Sep. 2001.*

Tsigarida et al. J. Applied Microb. 89(6): 901-909; Dec. 2000.*

Paster et al. "Inhibitory effect of oregano and thyme essential oils on moulds and foodborne bacteria", Letters in Applied Microbiology. vol. 11, No. 1, p. 33-37, 1990.*

"Powerful Antioxidant", International Food Ingredients (3)—May 2000, p. 49 (abstract only).*

* cited by examiner

*Primary Examiner*—Keith Hendricks
(74) *Attorney, Agent, or Firm*—MacCord Mason PLLC

(57) ABSTRACT

An improved food product having reduced levels of harmful bacteria. The food product includes an effective dose of an inhibitor for reducing the presence of harmful bacteria in the food. The inhibitor is an effective dose of the extract of labiatae plants. In the preferred embodiment, the food also includes an effective dose of bifidobacteria. For example, the bacteria may be selected from the group consisting of: *BifidoBacterium breve; BifidoBacterium longum; BifidoBacterium bifidum;* and *BifidoBacterium infantis.*

10 Claims, 1 Drawing Sheet

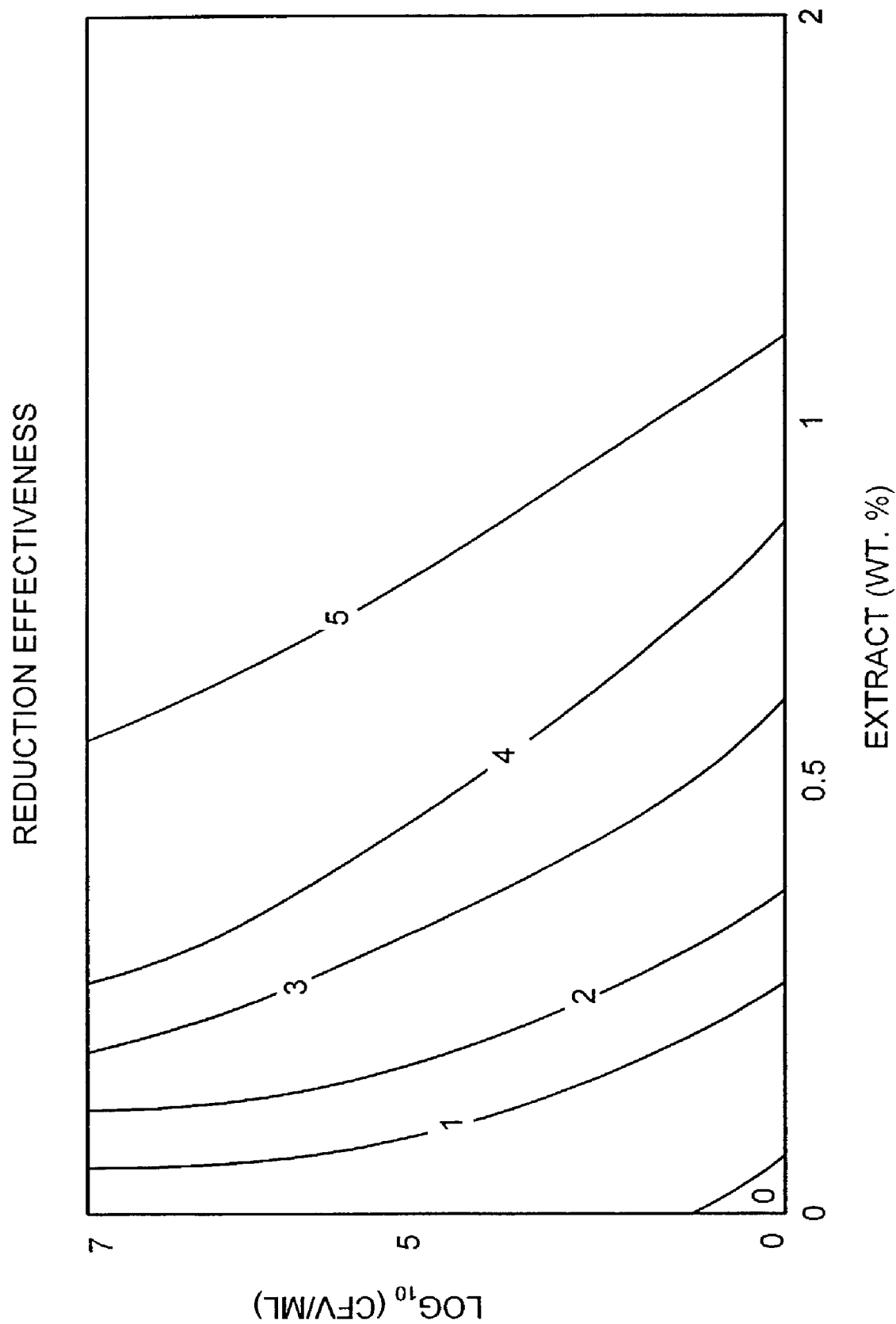

COMPOSITION AND METHOD FOR INHIBITION OF HARMFUL BACTERIA

This application claims benefit of provisional application 60/355,869 filed Nov. 30, 2001.

BACKGROUND OF THE INVENTION (1) Field of the Invention

The present invention relates generally to food products and, more particularly, to a composition and method for reducing the presence of harmful bacteria in food and water.

(2) Description of the Prior Art

The Pathogen Reduction Program of the U.S. Department of Agriculture Food Safety and Inspection Service recommends natural anti-microbial treatments for reducing or inactivating pathogenic bacteria in foods. The overall goal of this program is to develop a procedure to achieve at least 5-log CFU reduction of *Escherichia coli* O157:H7 in meat products.

*Escherichia coli* O157:H7 is one of the leading causes of bacterial foodborne disease outbreaks in the United States. An estimated 73,000 cases of infection and 61 deaths occur each year. Many of these outbreaks are associated with the consumption of meat and meat products such as ground beef and ground beef patties.

Origanox™ is the tradename for the plant extract of Labiatae family of herbs manufactured by RAD Natural Technologies of Kiryat-Ono, Israel, and used as natural antioxidant in many food products. It is believed that it acts as a radical scavenger and prevents the development of lipid oxidation in foods. Other research work has shown that spices can act as anti-microbial agents. For example, spices have historically been added to many meat products to improve the quality and shelf life. However, it is not known which spices, their active ingredients or how much is effective.

Thus, there remains a need for a new and improved composition and method for reducing the presence of harmful bacteria in food and water.

SUMMARY OF THE INVENTION

The present invention is directed to an improved food product having reduced levels of harmful bacteria. The food product includes an effective dose of an inhibitor for reducing the presence of harmful bacteria in the food. The inhibitor is an effective dose of the extract of labiatae plants.

In the preferred embodiment, the food also includes an effective dose of bifidobacteria. For example, the bacteria may be selected from the group consisting of: *BifidoBacterium breve; BifidoBacterium longum; BifidoBacterium bifidum;* and *BifidoBacterium infantis*. It has been found that the effective dose of said bacteria is between $10^5$ and $10^7$ CFU/ml.

In the preferred embodiment, the food product is selected from the group consisting of: animal products; plant products; and water. For example, the animal products include meat and dairy products, specifically ground beef. The plant products may include leaves, stalks, fruit, and juices.

In the preferred embodiment, the extract of the labiatae plants is water-soluble and is formed as a powder. Also, in the preferred embodiment, the effective dose is greater than about 0.1% by weight of the food with between about 0.1% and 2% by weight of the food being preferred. In the most preferred embodiment, the effective dose is about 0.5% by weight of the food.

These and other aspects of the present invention will become apparent to those skilled in the art after a reading of the following description of the preferred embodiment when considered with the drawings.

BRIEF DESCRIPTION OF THE DRAWINGS

FIG. 1 illustrates the effectiveness in reduction of *E-Coli* as a function of wt. % of plant extract and CFU/ml of BifidoBacterium.

DESCRIPTION OF THE PREFERRED EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawing, it will be understood that the illustration is for the purpose of describing a preferred embodiment of the invention and are not intended to limit the invention thereto.

*Escherichia coli* O157:H7 (380–94) were allowed to grow at 37° C. for 8 hours in BHI media containing Origanox™ plant extract at various concentrations (0.0, 0.5, 1.0, and 1.5% W/V). Samples were withdrawn at different time interval of 0, 1, 2, 4, 6, 8 hours and surface plated on BHI agar. Plates were incubated at 37° C. for 24 hours. Results showed that addition of Origanox™ plant extract caused a significant reduction in the growth rate of the pathogenic bacteria ($P<0.05$) and is an effective anti-microbial agent. Results also suggest that combinations of other techniques such as irradiation or ozonation along with the plant extract with may provide a synergistic effect to make our food safe.

While not known at this time, it is believed that Manganese ($Mn^{2+}$) is the common element in the treatment agents. It is believed that Manganese could stimulate the production of acids and anti-microbial compound of lactic acid bacteria. Therefore, the combination of starter culture and spices would enhance the biosafety of these consumable products.

Tests were then conducted to determine the effectiveness of combinations of bifidobacteria and spices on inactivation of *E. coli* O157:H7 in ground beef stored at 37 C. Ground Beef (93% lean meat) was inoculated with *Escherichia coli* O157:H7 (380–94) to make the initial inoculum level of 2 log cfu/g. Inoculated ground beef was mixed with different spices (garlic, ginger, jalapeno pepper and Origanox™ plant extract, a commercial spice served as antioxidant) at the level of 2%(W/V). Bifidobacteria can then added to a final level of 5-log cfu/g. Samples were stored at 37° C., collected at 0, 24 and 48 hours, stomached for 120 seconds, serial diluted, and plated onto EMB agar plates. Plates were incubated at 37° C. for 24 hours.

The results showed that ground beef treated with Origanox™ plant extract had the highest inhibitory effect against *E. coli*, followed by jalapeno pepper and garlic. Ginger had little effect on the growth of *E. coli*. The synergistic effect of spices and bifidobacteria on *E. coli* O157:H7 was higher than the effect of single spices alone ($P<0.05$).

Certain modifications and improvements will occur to those skilled in the art upon a reading of the foregoing description. It should be understood that all such modifications and improvements have been deleted herein for the sake of conciseness and readability but are properly within the scope of the following claims.

I claim:

1. An improved food product, said food product comprising:
    (a) a food;
    (b) an extract of labiatae plants in an amount of between about 0.1% and about 2% by weight of the food for reducing the presence of pathogenic bacteria in said food; and
    (c) bifidobacteria.

2. The food product according to claim 1, wherein said bacteria is selected from the group consisting of: *BifidoBacterium breve; BifidoBacterium longum; BifidoBacterium bifidum*; and *BifidoBacterium infantis*.

3. The food product according to claim 1, wherein said bacteria are present in an amount of between $10^5$ and $10^7$ CFU/ml.

4. The food product according to claim 1, wherein said food product is selected from the group consisting of: animal products; plant products; and water.

5. The food product according to claim 4, wherein said animal products comprises meat products, or dairy products, or combinations thereof.

6. The food product according to claim 5, wherein said meat product is ground beef.

7. The food product according to claim 4, wherein said plant products comprises leaves, stalks, fruit, or juices, or combinations thereof.

8. The inhibitor according to claim 1, wherein said extract is water soluble.

9. The inhibitor according to claim 8, wherein said extract is a powder.

10. A method for preparing an improved food product, said method comprising the steps of:
    (a) providing a food; and
    (b) adding an extract of labiatae plants in an amount of between about 0.1% and about 2% by weight of the food for reducing the presence of pathogenic bacteria in said food; and bifidobacteria.

* * * * *